United States Patent [19]

Askanazi et al.

[11] Patent Number: 5,294,642

[45] Date of Patent: *Mar. 15, 1994

[54] METHOD FOR IMPROVING VENTILATION DURING SLEEP AND TREATING SLEEP RELATED VENTILATION ABNORMALITIES

[75] Inventors: Jeffrey Askanazi, Haworth, N.J.; Susan Trimbo, Evanston, Ill.

[73] Assignee: Clintec Nutrition Co., Deerfield, Ill.

[*] Notice: The portion of the term of this patent subsequent to May 21, 2008 has been disclaimed.

[21] Appl. No.: 582,527

[22] Filed: Sep. 14, 1990

Related U.S. Application Data

[63] Continuation-in-part of Ser. No. 443,765, Nov. 30, 1989, Pat. No. 5,017,616.

[51] Int. Cl.$^5$ ............................................. A61K 31/195
[52] U.S. Cl. ....................................................... 514/561
[58] Field of Search ................................ 514/561, 923

[56] References Cited

U.S. PATENT DOCUMENTS 4,767,785 8/1988 Georgieff ............................ 514/561
5,017,616 5/1991 Askanazi ............................. 514/561

OTHER PUBLICATIONS

C. Weissman et al., Amino Acids and Respiration, Annals of Internal Medicine, vol. 98, No. 1, Jan. 1983, pp. 41–44.
J. Takala et al., Changes in Respiratory Control Induced by Amino Acid Infusions, Critical Care Medicine, vol. 16, No. 5, May 1988, pp. 465–469.
J. Askanazi et al., Effect of Protein Intake on Ventilatory Drive, Anesthesiology, v 60, No. 2, Feb. 1984, pp. 106–110.
A. Fein et al., Reversel of Sleep Apnea in Uremia by Dialysis, ARch Intern Med, vol. 147, Jul. 1987, pp. 1355–1356.
R. Milliman et al., Sleep Apnea in Hemodialysis Patients: The Lack of Testosterone Effect on its Pathogenesis, Nephron 40: 407–410 (1985).
P. Kimmel et al., Sleep Apnea Syndrome in Chronic Renal Disease, The American Journal of Medicine, vol. 86, Mar. 1989, pp. 308–314.
D. Prezant, Effect of Uremia and its Treatment of Pulmonary Function, Lung (1990) 168:1–14.
R. Evans et al., The Quality of Life of Patients with End-Stage Renal Disease, The New England Journal of Medicine, vol. 312, No. 9, Feb. 28, 1985, pp. 553–559.
Rote Liste (1987) pp. 56.
Soltesz et al., Blood Glucose and Plasma Amino Acid Concentrations in Infants of Diabetic Mothers, PEDIATRICS, vol. 61, No. 1, Jan. 1978, pp. 77–82.
Schultz et al., The Effect of Birth Asphyxia on Plasma Free Amino Acids in Preterm Newborn Infants, Acta Paediatrica Academiae Scientiarum Hungaricae, vol. 18 (2), pp. 123–130 (1977).

Primary Examiner—Frederick E. Waddell
Assistant Examiner—Raymond J. Henley, III

[57] ABSTRACT

A method for improving ventilation during sleep and treating sleep-related ventilation abnormalities. To this end, the present invention provides a method of using branched-chain amino acids as an effective therapy for sleep apnea. The branched-chain amino acid composition can be administered either parenterally or enterally, and can be administered alone or in combination with other nutrients. The branched-chain amino acid composition of the present invention functions as a ventilatory stimulator during sleep and does not result in any adverse effects either to the patient or to the sleep patterns of the patient. Preferably, the branched-chain amino acids comprise 60 to 85% of an amino acid solution that is administered to the patient.

12 Claims, 1 Drawing Sheet

METHOD FOR IMPROVING VENTILATION DURING SLEEP AND TREATING SLEEP RELATED VENTILATION ABNORMALITIES

This is a continuation-in-part of U.S. patent application Ser. No. 443,765 filed on Nov. 30, 1989 now U.S. Pat. No. 5,017,616.

BACKGROUND OF THE INVENTION

The present invention relates to a method for the use of branched-chain amino acids to improve ventilation during sleep. More specifically, the present invention relates to a method for treating sleep related ventilation problems, such as apnea.

Sleep apnea is recognized as a serious and often life threatening abnormality of the breathing pattern. See, Kales, et al, *Sleep Disorders: Sleep Apneas and Narcolepsy*. Ann. Intern. Med., 106:434–443, 1987. The morbidity of sleep apnea is due to a decrease oxygenation of the arterial blood and carbon dioxide retention secondarily to alveolar hypoventilation.

The condition of sleep apnea has been defined as the cessation of breathing for at least 10 seconds, that occurs at least 30 times during a 7 hour period of sleep. This definition, however, is based on sleep laboratory studies and accordingly, is not clinically applicable. Instead, arterial oxygen desaturation during sleep is the critical factor in determining sleep apnea. See, Block, et al, *Sleep Apnea. Hypopnea and Oxygen Desaturation in Normal Subjects*, New England Journal of Medicine, 300:513–517, 1979.

The sleep apnea syndrome has been observed as a primary disease in otherwise healthy subjects. Apneas can be divided into three sub-groups: central; obstructive; and mixed. Abnormal respiratory control is believed to be involved in all types of sleep apneas. Apneic breathing patterns during sleep occur also in association with certain other conditions, such as: morbid obesity; coronary disease; and congestive heart failure. See, Walse, et al, *Upper Airway Obstruction in Obese Patients With Sleep Disturbances and Somnolence*, Ann. Intern. Med. 76: 185–192, 1972; DeOlazabal, et al, *Disordered Breathing and Hypoxia During Sleep in Coronary Artery Disease*, Chest, 82:548–552, 1982; and Dark, et al, *Breathing Pattern Abnormalities and Arterial Desaturation During Sleep in the Congestive Heart Failure Syndrome, Improvement Following Medical Therapy*, Chest, 91:833–836, 1987, Patients recovering from anesthesia also frequently exhibit apneic breathing patterns.

Most patients with sleep apnea snore heavily and many exhibit severe oxygen desaturation. Oxygen desaturation during sleep may be associated with pulmonary and systematic hypertension and cardiac arrhythmias. Tilkian, et al, Sleep-Induced Apnea Syndrome, *Prevalence of Cardiac Arrhythmias and Their Reversal After Tracheostomy*. Am. J. Med. 63(3):348–358, 1976; and Tilkian, et al, *Hemodynamics in Sleep-Induced Apnea*, Am. Intern. Med. 85(6):714–719, 1977.

The typical management of sleep apnea syndrome is to relieve upper air obstruction and to also stimulate respiratory activity. Typically, pharmacologic techniques are utilized to achieve these goals. However, drug therapy alone is not usually effective in relieving sleep apneas. Moreover, such drug therapies are often associated with adverse side effects.

One drug that is used is Medroxyprogesterone acetate (MPA). MPA has been found to be a moderate, sustained ventilatory stimulant in man. MPA reduces sleep apnea in less than half of all patients. Strohl, et al, *Progresterone Administration and Progressive Sleep Apneas*, J.A.M.A., 245:1230–1232, 1981. But, MPA causes impotence in men and therefore the desirability and use of this drug is limited.

Another drug, protiptyline has been found to improve sleep apnea in some patients. This drug, however, is associated with such serious side effects such as: constipation; urinary retention; ataxia; and confusion. Brownell, et al, *Protiptyline in Obstructive Sleep Apnea*. New England Journal of Medicine, 307:1037–1042, 1982.

Accordingly, although pharmacologic interventions can be, in some cases, effective in decreasing the frequency and duration of sleep apneas, and the extent of oxygen desaturation in patients, the usefulness of such drug therapy is limited due to the adverse side effects of such drugs. Therefore, there is a need for an improved therapy for treating patients with sleep apnea.

Sleep apnea has also become of increasing clinical interest in chronic renal failure patients. See: Millman et al, *Sleep Apnea in Hemodialysis Patients: The Lack of Testerone Effect On Its Pathogenesis*, Nephron 1985:40:407–10; Fein et al, *Reversal of Sleep Apnea In Uremia by Dialysis*. Arch. Internal Med. 1987:147:1355–56; and Kimmel et al, *Sleep Apnea Syndrome In Chronic Renal Disease*. Am. J. Med. 1989:86:308–14.

In chronic renal patients, two separate forms of sleep apnea occur: a) obstructive apnea (wherein there is no airflow but respiratory effort); and b) central apnea (wherein there is no airflow and no respiratory effort). The detrimental clinical effects of sleep apnea can include arterial oxygen desaturation, cardiac arrhythmias, and pulmonary and systemic hypertension. The results of sleep apnea extend to the awake state and include excessive day-time sleepiness, mood and personality disorders as well as impaired intellectual function.

Improvements in both physiology and symptomology have been reported with different pharmacological agents. See: Parish, et al, *Cardiovascular Effects of Sleep Disorders*, Chest 1990:97:1220–26; NHLBI Workshop Summary, *Respiratory Disorders of Sleep, Patho-Physiology, Clinical Implications and Therapeutic Approaches*, Am Rev. Respir. Dis. 1987:136:755–61; and Douglas et al, *Breathing During Sleep In Patients With Obstructive Lung Disease*. Am. Rev. Respir. Dis. 1990:141:1055–70. However, common side effects such as peripheral neuropathy, paresthesia, acidosis, impotence, and dry mouth have limited the long-term application of these agents. Additionally, pharmacological intervention typically worsens the quality of the patient's sleep.

SUMMARY OF THE INVENTION

The present invention provides a method for improving ventilation during sleep. To this end, the present invention provides a method of using branched-chain amino acids as an effective therapy for sleep apnea. The branched-chain amino acid composition can be administered either parenterally or enterally, and can be administered alone or in combination with other nutrients. The branched-chain amino acid composition of the present invention functions as a ventilatory stimulator during sleep and does not result in any adverse effects either to the patient or to the sleep pattern of the patient.

In an embodiment, preferably, the branched-chain amino acids comprise 60 to 85% of an amino acid solution that is administered to the patient.

In an embodiment of the present invention, the composition comprises, per 100 ml, approximately 1.30 grams of Isoleucine, 1.38 grams of Leucine, and 1.24 grams of Valine.

In an embodiment of the method of the present invention, approximately 4 grams of branched-chain amino acids are administered per hour.

In an embodiment, a method for treating sleep apnea in a chronic renal failure patient is provided, the method comprising administering to a patient an effective amount of an amino acid solution including branched chain amino acids. The amino acid solution can be administered parenterally, enterally, or through the peritoneal.

Additional features and advantages of the present invention are described in, and will be apparent from, the detailed description of the presently preferred embodiments and the drawings.

DETAILED DESCRIPTION OF THE PRESENTLY PREFERRED EMBODIMENTS

Figure 1:
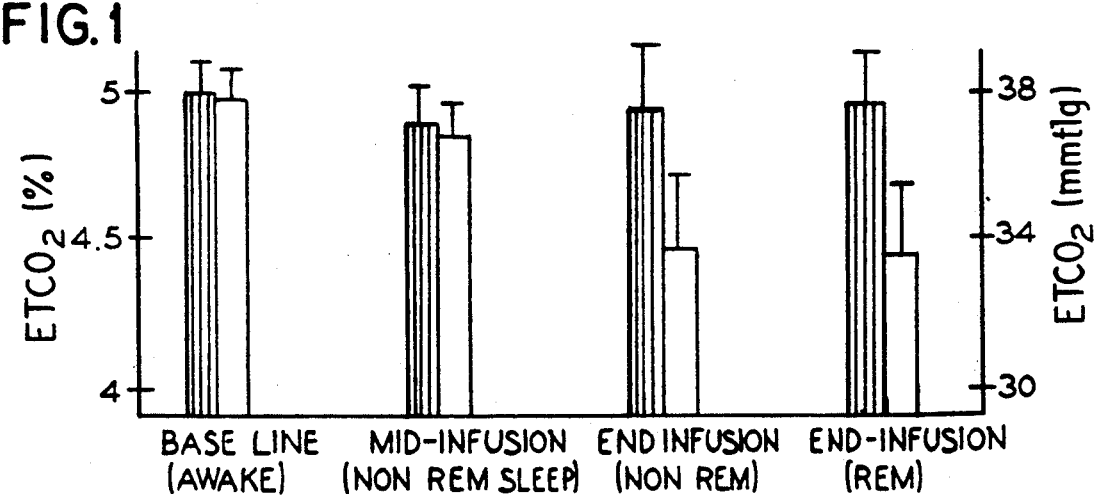
FIG. 1 illustrates, graphically, end-tidal (EtCO$_2$) during nocturnal infusion of a saline and a 4% branched-chain amino acid solution.

Branched-chain amino acid infusions have been shown to increase ventilatory drive when compared to conventional amino acid solutions and 5% dextrose. The infusion of amino acids increases ventilation by shifting the response curve of minute ventilation to arterial carbon dioxide tension to the left during carbon dioxide inhalation.

The inventor of the present invention has found that by altering an amino acid composition, by increasing the amount of branched-chain amino acids, an increase in ventilation and a decrease in arterial carbon dioxide tension is achieved. Branched-chain amino acids induce a larger decrease in arterial carbon dioxide tension and a larger increase in ventilatory response to carbon dioxide than a conventional amino acid solution. It has been found that branched-chain amino acids will induce a larger decrease in arterial carbon dioxide tension and a larger increase in ventilatory response to carbon dioxide than a conventional amino acid solution when infused for four hours after an overnight fast. This affect is even more dramatic when the infusion is continued over a 48 hour period.

By way of example, and not limitation, examples of the present invention will now be set forth.

EXAMPLES

Example 1

Five non-smoking healthy male volunteers (24 to 32 years of age), with no sleep disorders and who were not taking any medication, were studied. The subjects were studied on three separate nights. One night was a control that did not include the infusion of any solution and on the other two nights a continuous infusion of either BCAA (3.5% solution of 100% BCAA) or placebo (½ normal saline) was administered. The composition of the BCAA solution used was as follows:

| Composition Of BCAA Solution (per 100 ml) | |
|---|---|
| Isoleucine | 1.38 g |
| Leucine | 1.38 g |
| Valine | 1.24 g |
| Total nitrogen | 443 mg |

The BCAAs/saline solutions were infused in a single blind crossover design with infusion/control nights randomly assigned within every patient. The patients were allowed no food intake after 5 pm and no stimulants (i.e., coffee) were allowed after 12 noon on the study days.

The subjects were admitted at 8:30 p.m. to a sleep-awake center. On the nights they were to receive an infusion, a peripheral cannula was inserted into the patients for the infusion. Sleep stages were studied using a 12-channel polysomnographic monitor (Grass P78). Chest wall movements were measured with a pneumograph consisting of a small circular rubber bellows attached around the chest. The bellows were connected to a volumetric pressure transducer. The signals were amplified with a DC amplifier. Air flow at the mouth and nose was measured by a thermistor placed at each nostril and the upper lip in the midline position. An ear oximeter (Ohmeda Biox 3700) was used to record oxyhemoglobin saturation. End tidal CO$_2$ was measured using a capnograph (Normocap, Datex, Finland), the sampling tube was placed in the nasopharynx. A continuous electrocardiogram ran during the night.

The infusion solutions were started one hour prior to the estimated bedtime. The infusion rate was 100 ml/hour and infusion was discontinued in the morning at 7:30 a.m. The BCAA dose was 4 grams of amino acids/hour responding 0.443 grams of nitrogen/hour.

The end-tidal CO$_2$ levels during nights of BCAA infusion (44±5 mmHg) were lower than during control nights (C: 52±1 mmHg, $p<0.01$ and S: 50±3 mmHg, $p<0.05$). There was a trend ($p<0.2$) of increase in O$_2$-saturation levels. The results are set forth in Table 1 below:

TABLE 1

The highest end-tidal CO$_2$ (ETCO$_2$), and lowest SaO$_2$ values during the study nights; C (control nights without infusion), BCAA and NaCl

|  | C | BCAA | NaCl |
|---|---|---|---|
| ETCO$_2$ (mmHg) | 52 ± 1.4 | 44 ± 5.3 | 50 ± 2.6 |
| SaO$_2$ (%) | 93 ± 1.6 | 95 ± 2.3 | 94 ± 0.5 |

There was no significant change in the amount of REM sleep. The amount of stage 3 sleep and the combined stage 3 & 4 sleep were greater during BCAA nights than control nights (7.2±4.0% vs 4.3±2.8%, $p<0.05$ and 15.9±3.0% vs. 12.3±3.9%, $p<0.02$, respectively). Sleep efficiency was slightly, but not significantly, decreased with either infusion (BCAA:87±8, NaCl:87±8, and C:92±10). One patient had 10 apneic episodes on the control night, 5 with NaCl, but none with BCAA infusion. The polysomnographic data is summarized in Table 2 below:

TABLE 2

| The polysomnograph data from the three study nights | | | |
|---|---|---|---|
| | C | BCAA | NaCl |
| Sleep efficiency | 92 ± 10 | 87 ± 8 | 87 ± 8 |
| Sleep latency | 2.1 ± 3.2 | 4.7 ± 4.9 | 2.1 ± 1.5 |
| Stage 1 sleep | 3.2 ± 2.3 | 5.3 ± 5 | 4.5 ± 1.8 |
| Stage 2 sleep | 59 ± 3.7 | 59 ± 3.2 | 62 ± 5.5 |
| Stage 3 sleep | 4.3 ± 2.8 | 7.2 ± 4 | 9 ± 6 |
| Stage 4 sleep | 8 ± 6 | 7 ± 3 | 6 ± 5 |
| Stage 3 & 4 | 12 ± 4 | 16 ± 3 | 15 ± 9 |
| REM sleep | 25 ± 6 | 20 ± 5 | 19 ± 4 |
| REM latency | 80 ± 36 | 95 ± 109 | 73 ± 17 |
| Apneas | 2.5 ± 5 | 0 ± 0 | 1.3 ± 2.5 |
| Hypopneas | 7 ± 11 | 4 ± 6 | 4 ± 6 |

All subjects had slightly hypercapnic highest end-tidal $CO_2$ values during both control nights and BCAA infusion decreased it to eucapnic levels (range 44–36 mmHg). BCAA infusions did not cause hypocapnia and thus the risks of causing hyperventilation and respiratory alkalosis appears negligible. There was not a significant change in oxygen $SaO_2$ during BCAA infusion, which was to be expected as all patients were in good health and had normal saturation levels (range for lowest value was 93–99%). One subject had apneas during control nights but not during BCAA infusion. Although some investigators have indicated that the hypoxic ventilatory drive is more important in sleep apnea patients than hypercapnic ventilatory drive, the results indicate enhancing the respiratory drive by BCAA infusion assists in normalizing the breathing patterns during sleep in healthy subjects.

The sleep patterns, even with the infusion of BCAAs, remained largely intact. There was no significant change in the amount of REM sleep or REM latency. The amount of stage 3 sleep and combined stage 3 & 4 sleep increased significantly during BCAA nights when compared to control night without infusion. The study demonstrates that BCAA infusions indeed affect neurophysiological functions during sleep. The accentuation of the respiratory effects of amino acids by BCAA can have important clinical relevance for patients with decreased ventilatory drive due to anesthesia, medication, prolonged administration of 5% dextrose, or sleep apneas due to different origins.

Example No. 2

A 31 year old, morbidly obese white female was admitted with a diagnosis of increasing shortness of breath, peripheral cyanosis secondary to morbid obesity with a history of sleep disturbance (diagnosis: sleep apnea versus obesity hypoventilation). The patient had been previously maintained on home oxygen therapy and nasal CPAP. The patient presented increasing dyspnea on exertion of a half a block, four to five pillow orthopnea, frequent night awakenings, and chronic peripheral edema. The patient also had perioral and peripheral cyanosis, complained of feeling very tired in the mornings, and had a history of lightheadedness and diffuse constant chronic numbness in the morning.

During admission, the patient's blood gases were measured. The blood gases were arterial PO2 67 mmHg, arterial PCO2 50 mmHg and PH 7.34. Vital capacity was 1.1 liter (predicted 3.8), forced expiratory volume 0.81 liter (predicted 2.7).

A past medical history was taken and was significant in that a gastric stapling performed at St. Luke's eight years prior, had became "unbuttoned."

The medicines the patient was given, at the time of admission included Lasix and Aminophylin. The patient was also started on a 600 calorie diet. The patient's blood gases were: arterial PO2 46, arterial PCO2 51, PH 7.42 while awake.

The patient began a regimen of branched chain amino acid parenteral nutrition. The patient was started on a Branchamine infusion of 4%, available from Clintec Nutrition, Deerfield, Ill, at 100 ml/hr in the hospital. This was well tolerated. After the patient left the hospital, home infusions were instituted on a nightly basis at a rate of 100 ml/hr of 4% Branchamine, available from Clintec Nutrition. Soon thereafter, symptomatic improvement occurred.

Following nine months of these infusions, the patient remained stable at home, was more energetic upon awakening, and many of her morning symptoms had resolved completely. The patient's vital capacity had increased to 1.17 l and her FEV1 had increased to 0181 l/sec. Feelings of lightheadedness and other symptoms previously reported had improved as did the perioral and peripheral cyanosis the patient had experienced upon awakening.

The increase in vital capacity and FEV1 demonstrates that the Branchamine has improved the patient's sleep apnea.

Example No. 3

Seven chronic renal failure (CRF) patients (see Table 3 below) treated with hemodialysis three (3) times a week underwent nocturnal polysomnography and were studied on three nights prior to hemodialysis on the following day. Patients taking sedatives or antihistamines discontinued these drug during the study period. Six of the patients were on antihypertensive medications, including betablockers.

TABLE 3

| Patient Characteristics (n = 6). Mean ± SD. | | |
|---|---|---|
| | | [normal range] |
| Age | | |
| Sex | | |
| Weight (kg, after dialysis) | | [90–120%] |
| % of ideal body weight* | | |
| PH | | |
| PCO2 (mm Hg) | | |
| PO2 9 mm Hg) | | |
| HCO3– (mmol/l) | | |
| Sleep pattern | | |
| Stage 1 and 2 (%) | 66 ± 12 | [63 ± 9] |
| Stage 3 and 4% | 19 ± 9 | [12 ± 6] |
| REM sleep (5) | 14 ± 8 | [23 ± 4] |
| Sleep efficiency (%) | 70 ± 12 | [97 ± 2] |
| Sleep latency (min) | 21 ± 15 | [6 ± 4] |
| REM sleep latency (min) | 85 ± 40 | [85 ± 30] |

*% of ideal body weight is % of midpoint of medium frame range in the Revised Metropolitan Ideal Body Weight Tables (18 = 985) for persons aged 25 years and over. Definitions of terms used in Table:
Sleep efficiency = total sleep time divided with total recording time.
Sleep latency = the interval between lights out and sleep onset.
REM sleep latency = the period from sleep onset to the first epoch (30 seconds of REM sleep).

No food intake was allowed after 5 p.m. on the study nights. A peripheral line (22G) was inserted in the arm contralateral to the arterio-venous dialysis access. The first night was used as a control. Accordingly, the patients did not receive any infusion the first night.

After the first night, the patients were randomized to receive either branched-chain amino acids (60 mg/kg/h = 1.4 ml/kg/h, corresponding to 100 ml/h in a 70 kg person) or saline, intravenously, for 7 hours on the two (2) study nights. The maximum amount of protein infused was never greater than 35 g/patient. The BCAA solution (4% Branchamin-available from Baxter Healthcare Corporation, Deerfield, Ill.) contained 1.38 g each of isoleucine and leucine per 100 ml and 1.24 of valine per 100 ml. The infusions were started 1 hour before the patient's habitual bed-time, which was between 10.00 and 11.00 p.m. in all cases. In one patient, one of the study nights, on which branched chain amino acids were given, was repeated due to problems with venous access.

Surface electrodes and a 12 channel Grass P78 polysomnograph were used for the continuous recording of the electroencephalogram, submental electromyelogram, electro-oculogram, and electrocardiogram. Respiratory movements were monitored with pneumograph bellows around the chest and abdomen and were recorded on the polysomnograph. The pneumograph bellows were used in a semiquantitative manner to allow differentiation of obstructive and central apneas and hypopneas.

A finger oximeter (Ohmeda Biox 3700) and a capnograph (Normocap, Datex) were used to record oxyhemoglobin saturation ($SaO_2$) and $ETCO_2$ To measure $ETCO_2$ a length of thin tubing was inserted about 1 cm into the nostril of the patient and the other end was connected to the sample port of a capnograph. The capnograph was calibrated prior to each night's study. Both the oximeter and capnograph were connected to the polysomnograph for continuous recording. The presence of airflow was inferred by the $ETCO_2$ and by thermocouples at the nose and mouth.

The polysomnograms were scored for sleep stages and incidence, length, and severity of apneas/hypopneas by a registered polysomnographic technologist who was not made aware of the premise of the investigation. Following the traditional staging and scoring definitions, sleep was divided into REM (Rapid Eye Movement) sleep and non-REM sleep (Stage 1–4).

Obstructive apnea was defined as the absence of airflow in the presence of rib cage and abdominal excursions for a period of at least 10 seconds. Non-obstructive (central) apnea was defined as the absence of both airflow and respiratory movement for at least 10 seconds. Apneas with both obstructive and central characteristics ("mixed") were classified together with the obstructive apneas. Hypopnea was defined as an episode of at least 10 seconds in which the amplitude of the sum of ventilatory movement of rib cage and abdomen was less than 50% of the mean amplitude of the previous breaths. Five or more apneas per hour of sleep was considered abnormal and apnea associated with more than 5% desaturation was considered severe.

Analysis of $ETCO_2$, $SAO_2$, and respiratory and heart rate was carried out during blocks of 3–5 minutes of stable breathing (no apneas) in every sleep stage that was recorded during each hour of the sleep study. Only $CO_2$ polygraph waveforms consisting of a sharp upstroke and downstroke with a relatively flat plateau which had a slightly ascending slope were considered valid for analysis of $ETCO_2$. During each hour, the block selected for analysis was as close as possible to the middle of the hour. Thus, the measurements of breaths during each hour of sleep avoided potential bias associated with selecting breaths from only one point in time during the night of polysomnography.

The baseline consisted of a 5 minute block of stable breathing after the patient retired and before the onset of sleep. Mean values were obtained by averaging all measurements over 3 to 5 minute periods. Data from the baseline were compared to hourly measurements for midnight to 5 a.m. (this particular period was chosen since some patients did not fall asleep until midnight and many of them had to get up at 5 a.m. for early dialysis). The analyzed data from non-REM periods were for stage 1 and 2 because adequate data for stage 3 and 4 was missing in many patients (the patients had infrequent periods of REM sleep, which usually occurred at the end of the study period). Therefore, data from the last recorded REM period was used for comparison with baseline and non-REM values.

Statistical analysis was performed using Student's T-test (paired) and one-way analysis of variance (ANOVA) with the Tukey post-hoc test. A P value less than 0.05 was considered statistically significant.

Seven patients completed the three night study. Only one patient had severe sleep apnea. This patient was very different from the remaining patients both with respect to sleep and respiratory pattern, and is discussed separately. In the six patients without severe sleep apnea no significant changes in sleep quality and sleep stages, except for an increase in REM sleep, were found on the night of BCAA infusion (see Table 4 below).

TABLE 4

| Polysomnographic and respiratory data (n = 6). Mean ± SD. | | | |
|---|---|---|---|
|  | Saline | BCAA | P-Value |
| Stage 1 and 2 (%) | 65 ± 20 | 61 ± 13 | n.s |
| Stage 3 and 4 (%) | 21 ± 14 | 22 ± 11 | n.s |
| REM sleep (%) | 12 ± 10 | 19 ± 8 | P < 0.05 |
| Sleep efficiency (%) | 66 ± 16 | 74 ± 13 | n.s |
| Sleep latency (min) | 39 ± 35 | 12 ± 10 | P = 0.1 |
| REM latency (min) | 75 ± 57 | 109 ± 80 | n.s |
| Arousals (total) | 30 ± 12 | 35 ± 14 | n.s |
| Arousals (>5 min) | 5 ± 3 | 5 ± 2 | n.s |
| Apnea index (number/h of sleep) | 2 ± 2 | 2 ± 3 | n.s. |
| Apnea-Hypopnea index (number/h of sleep) | 3 ± 4 | 4 ± 5 | n.s |
| Baseline $SaO_2$ (%) | 97 ± 2 | 96 ± 1 | n.s |
| Lowest $SaO_2$ (%) | 90 ± 3 | 88 ± 5 | n.s |

Figure 2A:
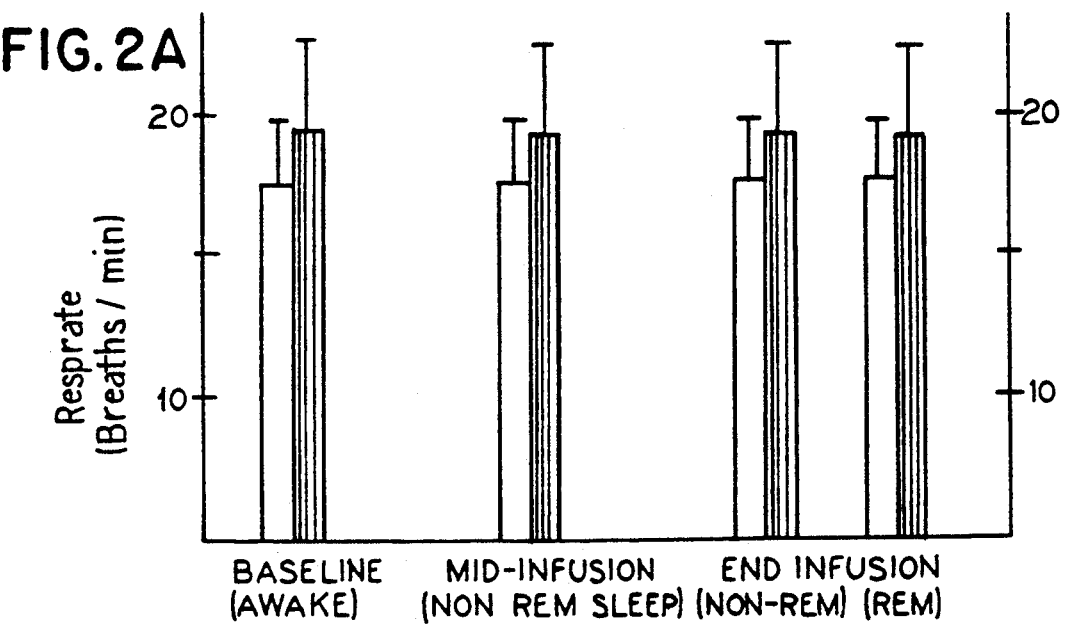
FIG. 2A and 2B illustrate graphically, a) resprate and b) arterial oxygen saturation (SaO$_2$) during a 7 hour nocturnal infusion of saline and a 4% branched-chain amino acid solution.
Figure 2B:
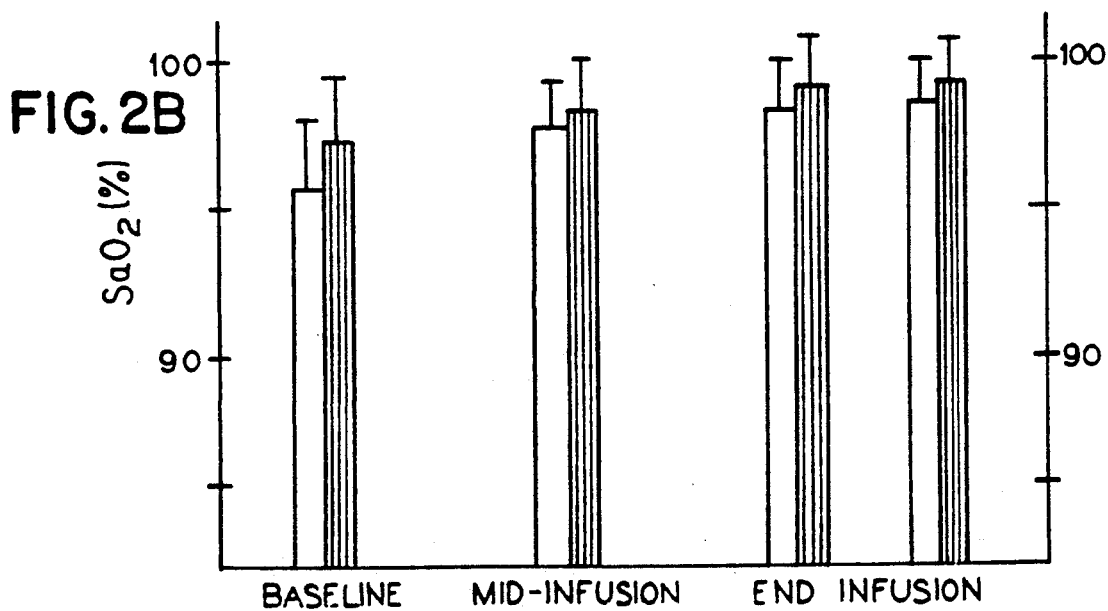

Baseline $ETCO_2$ for each night was compared with values for each hour during the night. On the placebo (saline) night no changes in $ETCO_2$ took place (see FIG. 1). As also illustrated in FIG. 1, with BCAA, however, there was a significant decrease (11%) in mean $ETCO_2$ during the 7 hour infusion both for non-REM (P<0.05) and REM sleep (P<0.05). Respiratory rate and oxygen saturation did not change significantly from baseline throughout the study nights (see FIG. 2), nor were there any significant changes in heart rate.

Patient #7 (see Table 5 below) had severe sleep apnea and also differed from the other patients in that he was overweight (150% of his ideal body weight). The patient had markedly reduced sleep efficiency on all nights (see Table 5).

Due to continuous arousals in connection with the apneas, Patient #7's sleep was scored as transitional sleep, type non-REM and REM. There was no significant increase in the ratio of REM to non-REM sleep when comparing the night of saline and BCAA, but the patient seemed to have longer arousals with BCAA (see Table 5). The BCAA night in this patient was also associated with a large decrease in the total number of obstructive apneas, corresponding to a fall in the apnea index from 85 to 31 (see Table 5). Furthermore, no central apneas occurred that night.

Because the decrease in apneas was not associated with a decrease in the number of hypopneas, the apnea-hypopnea index did not drop. However, the mean duration of both obstructive apneas and hypopneas was lower when comparing saline and BCAA (30 vs 36 seconds and 30 vs 20 seconds respectively). The change in apnea pattern was also associated with improvements in oxygen saturation (see Table 5). In addition to the difference in the lowest measured value of oxygen saturation, the time spent with oxygen saturation values less than 70% was also reduced on the BCAA night.

While the apneas during the saline night were associated with regular desaturations from a baseline of 95% down to around 40%, the majority of the apneas and hypopneas on the BCAA night only caused desaturation down to around 70%. On both nights the desaturation was worse during periods of REM sleep. Despite the improvements with BCAA, the severity of his sleep apnea made this patient a candidate for a trial of nocturnal Continuous Positive Airway Pressure (CPAP) mask and he was referred for this.

TABLE 5

Sleep and respiratory data for Patient #7 (male, 38 years old) that had severe obstructive sleep apnea.

| Night | Control | Saline | BCAA |
|---|---|---|---|
| Sleep efficiency (%) | 57% | 55% | 47% |
| Transitional sleep* | | | |
| non REM | 76% | 62% | 57% |
| REM | 17% | 23% | 17% |
| arousals | 7% | 15% | 24% |
| Total number apnea | 363 | 323 | 94 |
| obstructive | 360 | 319 | 94 |
| central | 3 | 4 | 0 |
| Apnea index | 81 | 85 | 31 |
| Total number hypopneas | 412 | 190 | 395 |
| Apnea/hypopnea index | 173 | 135 | 160 |
| Oxygen saturation (%) | | | |
| baseline | 97 | 94 | 96 |
| lowest | 40 | 34 | 54 |

*Transitional sleep = sleep continuously interrupted by arousals.

BCAA was associated with a significant decrease in the number of obstructive apneas. Further, substantially less desaturation was associated with the remaining apneas and hypopneas. The oximeter used had previously been tested for accuracy down to oxygen saturation levels of 40% and found reliable within 2-3%; accordingly, the decrease in $ETCO_2$ during BCAA infusion patients can be taken as a sign of increased respiratory drive and improved alevelor ventilation.

BCAA were found to both significantly improve respiratory drive, reflected by a decrease in $ETCO_2$, and to increase the amount of REM sleep. In the one patient with severe obstructive sleep apnea, BCAA reduced both the total number of apneas and the severity of desaturation in the remaining apneas and hypopneas.

The results indicate that BCAA may be of use in the treatment of sleep apnea in chronic renal failure patients. It is further noted that BCAA can be given without worsening the already disturbed sleep pattern in these patients.

Although the BCAA can be given both parenterally and enterally, in chronic renal patients, it may be desirable to give the BCAA intradialytic. This eliminates both practical problems of administration and eliminates the risk of fluid overloading.

In continuous ambulatory peritoneal dialysis patients, the BCAA can be given through the peritoneal. In such a case, preferably a maximum of 100 gms of BCAA should be administered.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method of treating sleep apnea in a chronic renal failure patient comprising:
    administering to a patient a therapeutically effective amount of an amino acid solution comprising branched-chain amino acids.

2. The method of claim 1 wherein the solution is administered parenterally.

3. The method of claim 1 wherein the solution is administered enterally.

4. The method of claim 1 wherein the solution is administered through the peritoneum.

5. A method of treating sleep apnea and improving quality of sleep in a chronic renal failure patient comprising:
    administering to a patient a therapeutically effective solution comprising approximately 60 to about 85% branched-chain amino acids.

6. The method of claim 5 wherein the solution is administered parenterally.

7. The method of claim 5 wherein the solution is administered enterally.

8. The method of claim 5 wherein the solution is administered through the peritoneum.

9. A method of treating sleep apnea, without adversely effecting the quality of sleep, in a chronic renal failure patient comprising:
    administering to a patient a therapeutically effective amount of an amino acid solution comprising: isoleucine, leucine, and valine.

10. The method of claim 9 wherein the solution is administered parenterally.

11. The method of claim 9 wherein the solution is administered enterally.

12. The method of claim 9 wherein the solution is administered through the peritoneum.

* * * * *